United States Patent
Wang

(10) Patent No.: US 6,884,781 B2
(45) Date of Patent: Apr. 26, 2005

(54) TREATMENT OF SHOCK USING ADRENOMEDULLIN BINDING PROTEIN-1

(76) Inventor: Ping Wang, 59 Highland Ave., Roslyn, NY (US) 11576

( * ) Notice: Subject to any disclaimer, the term of this patent is extended or adjusted under 35 U.S.C. 154(b) by 0 days.

(21) Appl. No.: 10/729,193

(22) Filed: Dec. 5, 2003

(65) Prior Publication Data

US 2004/0229789 A1 Nov. 18, 2004

Related U.S. Application Data

(63) Continuation-in-part of application No. 10/439,762, filed on May 16, 2003.

(51) Int. Cl.[7] .......................... A61K 38/00; A61K 38/43
(52) U.S. Cl. .......................... 514/12; 424/94.1; 435/183
(58) Field of Search ...................... 435/183; 424/94.1; 514/12

(56) References Cited

PUBLICATIONS

Yang et al., Mechanisms of the beneficial effect of adrenomedullin and adrenomedullin–binding protein–1 in sepsis: Down regulation of proinflammatory cytokines, 2002, Critical Care Medicine, 30(12), 2729–35.*

Elsasser T.H. et al., "Adrenomedullin binding protein in the plasma of multiple species: characterization by radioligand blotting"; Endocrinol 140:4908–4911, 1999.

Shindo T. et al., "Hypotension and resistance to lipopolysaccharide–induced shock in transgenic mice overexpressing adrenomedullin in their vasculature"; Circulation 101:2309–2316, 2000.

Wichterman K.A. et al., "Sepsis and septic shock: a review of laboratory models and a proposal"; J Surg Res 29:189–201, 1980.

Wu R. et al., "Adrenomedullin and adrenomedullin binding protein–1 downregulate TNF–alpha in macrophage cell line and rat Kupffer cells"; Regul Pept 112:19–26, 2003.

Yang S et al., "Novel approach to prevent the transition from the hyperdynamic phase to the hypodynamic phase of sepsis: The role of adrenomedullin and adrenomedullin binding protein–1"; Crit Care Med. 29 (12, Suppl.); abst. A12, Dec. 2001.

Yang S. et al., "Novel approach to prevent the transition from the hyperdynamic phase to the hypodynamic phase of sepsis: Role of adrenomedullin and adrendomedullin binding protein–1"; Ann Surg 236:625–633, 2002.

Yang S. et al., "Mechanisms of the beneficial effect of adrenomedullin and adrenomedullin–binding protein–1 in sepsis: down–regulation of proinflammatory cytokines"; Crit Care Med 30:2729–2735, 2002.

* cited by examiner

Primary Examiner—Robert A. Wax
Assistant Examiner—Suzanne M. Mayer
(74) Attorney, Agent, or Firm—Amster, Rothstein & Ebenstein LLP

(57) ABSTRACT

Methods of treating a mammal in shock or at risk for shock are provided. The methods involve administration of an adrenomedullin binding protein-1 to the mammal. Also provided are methods of preventing or treating a physiologic effect of shock in a mammal. These methods also involve administration of an adrenomedullin binding protein-1 to the mammal.

20 Claims, 1 Drawing Sheet

TREATMENT OF SHOCK USING ADRENOMEDULLIN BINDING PROTEIN-1

CROSS-REFERENCE TO RELATED APPLICATION

This is a continuation-in-part of application Ser. No. 10/439,762, filed May 16, 2003, incorporated by reference in its entirety.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant Nos. RO1 GM57468, GM53008, and KO2 A101461, awarded by the National Institutes of Health.

BACKGROUND OF THE INVENTION (1) Field of the Invention

This invention generally relates to treatment of shock. More specifically, the invention is directed to the administration of adrenomedullin binding protein-1 to mammals in shock or at risk for shock.

(2) Description of the Related Art

References Cited

Elsasser T H, Kahl S, Martinez A, Montuenga L M, Pio R, Cuttitta F: Adrenomedullin binding protein in the plasma of multiple species: characterization by radioligand blotting. *Endocrinol* 140:4908–4911, 1999.

Shindo T, Kurihara H, Maemura K, Kurihara Y, Kuwaki T, Izumida T, Minamino N, Ju K H, Morita H, Oh-hashi Y, Kumada M, Kangawa K, Nagai R, Yazaki Y: Hypotension and resistance to lipopolysaccharide-induced shock in transgenic mice overexpressing adrenomedullin in their vasculature. *Circulation* 101:2309–2316, 2000.

Wichterman K A, Baue A E, Chaudry I H: Sepsis and septic shock: a review of laboratory models and a proposal. *J Surg Res* 29:189–201, 1980.

Wu R, Zhou M, Wand P: Adrenomedullin and adrenomedullin binding protein-1 downregulate TNF-α in macrophage cell line and rat Kupffer cells. *Regul Pept* 112:19–26, 2003.

Yang S, Zhou M., Chaudry I H: Novel approach to prevent the transition from the hyperdynamic phase to the hypodynamic phase of sepsis: Role of adrenomedullin and adrendomedullin binding protein-1. *Ann Surg* 236:625–633, 2002a.

Yang S, Zhou M, Gowler D E, Wang P: Mechanisms of the beneficial effect of adrenomedullin and adrenomedullin-binding protein-1 in sepsis: down-regulation of proinflammatory cytokines. *Crit Care Med* 30:2729–2735, 2002b.

Shock, or circulatory insufficiency leading to inadequate blood flow to vital organs, is a potentially life-threatening medical emergency that often leads to organ damage, cardiac arrest, respiratory failure and death.

Shock can be caused by heart problems (cardiogenic shock), conditions blocking blood flow to or from the heart (extracardiac obstructive shock), loss of fluids (hypovolemic shock), or abnormal flow of fluids into the tissues (distributive shock). These dysfunctions in circulation can in turn be caused by bacterial blood infection (septic shock), severe allergic reaction (anaphylaxis), trauma (traumatic shock), severe bleeding (hemorrhagic shock), or neurologic dysfunction causing abnormal opening of blood vessels (neurogenic shock). While any shock is serious, septic shock and hypovolemic shock are particularly important due to their frequency of occurrence and frequently inadequate treatment regimens.

Despite attempts to improve survival of septic patients with intensive medical care, including antibiotics, aggressive intravenous fluids, nutrition, mechanical ventilation, and surgical interventions, the mortality rate still ranges from 30% to 50%. Of clinical trials testing novel agents for the treatment of sepsis, only activated protein C has previously been demonstrated to significantly reduce mortality in patients with severe sepsis. The high morbidity and mortality attributed to sepsis could be due to the fact that mediators or factors responsible for the transition from the hyperdynamic phase to the hypodynamic phase of sepsis are not fully understood. Consequently, there is a progressive deterioration of cell and organ functions and even death of the host, which might be prevented by interventions directed against and/or modulating these mediators/factors. It is therefore important to investigate the subtle alterations in cellular function and mechanisms of pathophysiological changes during sepsis and develop novel therapeutic strategies. In this regard, experimental polymicrobial sepsis induced by cecal ligation and puncture (CLP) mimics many features of clinical sepsis-peritonitis and is associated with an early, hyperdynamic phase (characterized by increased cardiac output and tissue perfusion, decreased vascular resistance, hyperglycemia and hyperinsulinemia) followed by a late, hypodynamic phase (characterized by reduced cardiac output and tissue perfusion, increased vascular resistance, hypoglycemia and hypoinsulinemia). The CLP model of sepsis has been used extensively to study the pathophysiologic and immunologic alterations in sepsis.

Despite advances in the trauma management, a large number of patients with traumatic injury die of hypovolemic circulatory collapse due to severe hemorrhage. Irreversible circulatory shock induced by traumatic injury and blood loss represent a major clinical problem, particularly in combat casualties. Traumatic injury (often accompanied by severe blood loss) is the principal cause of death in patients aged 1–44 years and the overall leading cause of life-years lost in the United States. Traumatic injury accounts for 37 million emergency department visits, 2.6 million hospital admissions, and 150,000 deaths each year. The resulting loss of productive life years exceeds that of any other disease, with societal costs of $260 billion annually. In less than two decades, trauma will equal to or surpass communicable diseases as the leading worldwide cause of disability-adjusted life-years lost. Although more effective prevention measures will reduce the early deaths resulting from massive hemorrhage and central nervous system injury, the transition from the reversible to the irreversible hypovolemia, or circulatory collapse, appears to be responsible for the majority of late deaths after trauma and blood loss.

Shock generally progresses in four stages. The initial stage is characterized by cardiac output insufficient to meet the body's metabolic needs, but not otherwise low enough to produce significant symptoms. The patient is anxious and alert, with altered mental status, and increased respirations. In the second, or compensatory, stage the patient exhibits an increase in heart rate, an increase in cardiac output, and vasoconstriction. The third, or progressive, stage of shock is characterized by falling blood pressure, increased heart rate, oligoria, and increasing system dysfunction. In the fourth, or irreversible stage, death is inevitable. The patient in the irreversible stage exhibits myocardial depression and massive capillary dilation, with blood pooling in the extremities.

Adrenomedullin, a newly reported and potent vasodilatory peptide, is an important mediator involved in both physiological and pathological states. Human AM, a 52-amino acid peptide, was first isolated and reported in 1993. AM has a carboxy terminal amidated residue and a 6-member ring structure formed by an intramolecular disulfide bond near the amino terminus, and is available commercially. Rat adrenomedullin has 50 amino acids with 2 amino acid deletions and 6 substitutions as compared to human adrenomedullin. Adrenomedullin transcripts and protein are expressed in a large number of tissues, and circulating levels of adrenomedullin were observed under normal as well as pathophysiological conditions. Previous studies using the CLP model of sepsis have shown that up-regulation of adrenomedullin plays a major role in initiating the hyperdynamic response during the early stage of sepsis, and reduced vascular responsiveness to adrenomedullin appears to be responsible for the transition from the hyperdynamic phase to the hypodynamic phase during the progression of polymicrobial sepsis.

In 1999, Elsasser et al. reported that specific adrenomedullin binding proteins (AMBP) exist in the plasma of several species including humans. More recently, the binding protein AMBP-1 has been identified in human plasma and has been shown to be identical to human complement factor H. AMBP-1 enhances adrenomedullin-mediated induction of cAMP in fibroblasts, augments the adrenomedullin-mediated growth of a cancer cell line, and suppresses the bactericidal capability of adrenomedullin on *E. coli*.

Studies by Shindo et al. (2000) have shown that a chronic increase in vascular adrenomedullin production in transgenic mice is protective against circulatory collapse, organ damage, and mortality of endotoxic shock. It was previously unknown whether adrenomedullin+AMBP-1 down-regulates proinflammatory cytokines and, if so, whether the beneficial effects of adrenomedullin+AMBP-1 are due to this down-regulation.

It has been previously demonstrated that proinflammatory cytokines play a critical role in the initiation and progression of sepsis syndrome and that TNF-α, IL-1β and IL-6 are important mediators of hemodynamic, metabolic and immunologic alterations in the host during sepsis. Studies have also shown that circulating levels of TNF-α, IL-1β and IL-6 increase significantly in the early, hyperdynamic phase of sepsis and remain elevated in the late, hypodynamic phase of sepsis. Although adrenomedullin is up-regulated following stimulation with TNF-α and IL-1β, some studies have shown that adrenomedullin suppresses IL-1β-induced TNF-α production in vivo and suppresses the secretion of TNF-α and IL-6 from RAW 264.7 cells stimulated with endotoxin in vitro.

BRIEF SUMMARY OF THE INVENTION

The instant invention is based on the discovery that adrenomedullin binding protein-1 (AMBP-1) is limiting relative to adrenomedullin in shock, and addition of AMBP-1 beneficially reduces physiologic effects of shock.

Thus, in some embodiments, the invention is directed to methods of treating a mammal in shock or at risk for shock. The methods comprise administering an adrenomedullin binding protein-1 (AMBP-1) to the mammal in sufficient amount to reduce a physiologic effect of the shock.

In other embodiments, the invention is directed to methods of preventing or treating a physiologic effect of shock in a mammal. The methods comprise administering to the mammal an adrenomedullin binding protein-1 (AMBP-1) in sufficient amount to reduce the physiologic effect of the shock.

DETAILED DESCRIPTION OF THE INVENTION

Figure 1:
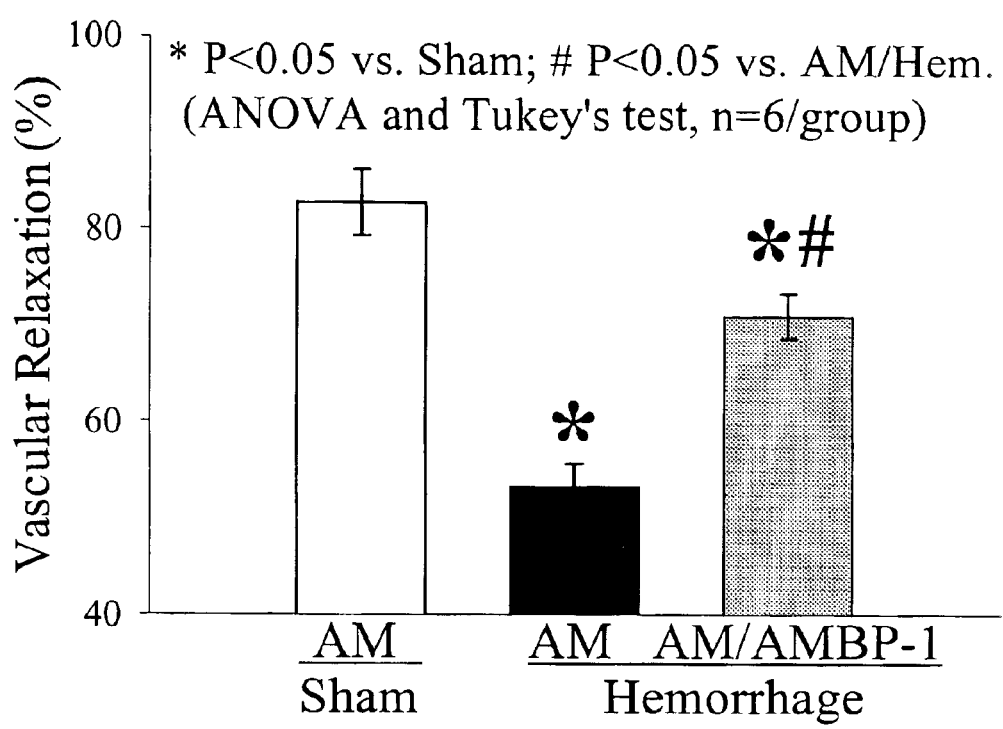
FIG. 1 is a graph of experimental data showing that administration of adrenomedullin (AM) with adrenomedullin binding protein-1 (AMBP-1) increases vascular relaxation in a rat model of hypovolemic shock.

The present invention is based on the discovery that adrenomedullin binding protein-1 (AMBP-1) is limiting relative to adrenomedullin during shock, which limits the effectiveness of adrenomedullin therapy for reducing deleterious effects of shock. Administration of AMBP-1 alleviates this adrenomedullin hyporesponsiveness and is thus a useful therapy for shock.

Thus, in some embodiments, the invention is directed to methods of treating a mammal in shock or at risk for shock. The methods comprise administering an adrenomedullin binding protein-1 (AMBP-1) to the mammal in sufficient amount to reduce a physiologic effect of the shock.

In these methods, the shock has an initial stage, a compensatory stage, and a progressive stage, which are physiologically distinguishable, as discussed above, under Background of the Invention. Although these three stages are believed to be present in all cases of shock, the duration of each stage can vary widely, depending on the severity and type of shock, such that it may be difficult to identify one or two of the stages.

AMBP-1 is preferably administered along with adrenomedullin, in order to maximize the therapeutic effect of the AMBP-1 administration.

These methods can be effectively used in any mammalian species, including experimental animals such as rat, mouse and guinea pig; domesticated animals such as horse, dog, pig, rabbit, cat and ferret; as well as humans.

The AMBP-1 and adrenomedullin administered in these methods can be from any mammalian species, but is preferably from the same mammalian species being treated, to minimize the possibility of allergic reactions to the treatment. Thus, a human can be treated with an AMBP-1 (and adrenomedullin, when desired) from any mammalian species, but treatment with the human forms of these proteins is preferred. The AMBP-1 and adrenomedullin can also be from the same or different species. AMBP-1 and adrenomedullin from numerous species have been cloned and sequenced. Examples include the following GenBank accessions: Y00716 (human AMBP-1), NM 130409 (rat AMBP-1), NM 009888 (mouse AMBP-1), AAH15961 (human adrenomedullin), AAH61775 (rat adrenomedullin), AAH52665 (mouse adrenomedullin), NP 776313 (cow adrenomedullin), S41600 (pig adrenomedullin), and BAA96494 (horse adrenomedullin). Using this information, the skilled artisan could identify AMBP-1 and adrenomedullin from any other mammalian species without undue experimentation.

The AMBP-1 or adrenomedullin for these methods could also be a synthetic protein, not identical to that from any species. The skilled artisan could identify numerous such proteins, using the sequence information provided in the above-identified GenBank accessions, by simply altering one of the above sequences by, e.g., substituting amino acid residues (or nucleotides encoding the amino acids) from one species into the sequence of another species. Additionally, the AMBP-1 or adrenomedullin can be a peptidomimetic or other known forms that are more resistant to degradation than the natural polypeptides. Examples include groups such as amides or ester groups attached to the peptides, since such protected peptides would be deprotected in vivo to deliver the active adrenomedullin and AMBP-1.

Synthesis of the AMBP-1 or adrenomedullin for these methods can be by any known method, e.g., synthesis by peptide synthetic methods or, preferably, expression from an expression vector in bacterial, yeast or mammalian cells.

These methods are useful for treatment of mammals undergoing, or at risk for, any type of shock, including cardiogenic shock, extracardiac obstructive shock, hypovolemic shock, distributive shock, septic shock, anaphylaxis, traumatic shock, hemorrhagic shock, and neurogenic shock. In preferred embodiments, the shock is hypovolemic shock (including hemorrhagic shock), traumatic shock, and septic shock.

Depending on the type and severity of shock, these treatments would be expected to beneficially reduce at least one physiologic effect of shock, including endothelial cell function, smooth muscle contractility, cardiac output, stroke volume, systemic oxygen delivery, regional blood perfusion, renal function, hepatic function, gut absorptive function, adrenal function, insulin responsiveness, lactic acidosis, hemoconcentration, total peripheral vascular resistance, or IL-10, TNF-$\alpha$, IL-1$\beta$ or IL-6 release.

The amount of AMBP-1 administered will depend on the size and condition of the patient. Generally, the dosage of AMBP-1 of 0.2 to 100 $\mu$g/kg body weight, including, for example, 0.5, 1, 2, 5, 10, 25, and 50 $\mu$g/kg, would be deemed appropriate, with the dosage on the low end of the dosage range being appropriate for the adult human. Where utilized, adrenomedullin of 0.1 to 50 $\mu$g/kg body weight, including, for example, 0.2, 0.5, 1, 2, 5, 10, and 25 $\mu$g/kg is appropriate. The compositions containing the active agents may be administered intravenously as a continuous drip. This is the most likely mode of administration, since these patients are generally hospitalized because of the gravity of their condition. The active agents are soluble, and would usually be administered in isotonic solutions such as Ringer's solution, buffered saline, etc. While liposomes may be prepared, such are usually not needed for protection when the agents are given by intravenous drip. However, the invention is not narrowly limited to any particular form of administration, and modes of administration other than continuous drip intravenous administration are within the scope of the invention. Because the peptides are water-soluble, it is possible to give them in aqueous solutions without addition of solubilizing agents.

The AMBP-1 can be administered prophylactically at any time before initiation of shock, for example, during or after a septic pregnancy or delivery, a trauma, a heart attack, or when anaphylaxis is feared. Alternatively, the AMBP-1 can be administered during the initial, compensatory, or progressive stage of shock. Preferably, the AMBP-1 is administered within 90 minutes of the initiation of the shock, to reduce or prevent organ damage caused by the shock. When adrenomedullin is also administered, it can be administered before, during, or after administration of the AMBP-1.

The AMBP-1 (and adrenomedullin) can also be administered in conjunction with another agent that reduces a physiological effect of the shock. Nonlimiting examples of such agents include vasodilators, vasopressors, corticosteroids, antibiotics, and opiates.

In other embodiments, the invention is directed to methods of preventing or treating a physiologic effect of shock in a mammal. The methods comprise administering to the mammal an adrenomedullin binding protein-1 (AMBP-1) in sufficient amount to reduce the physiologic effect of the shock. As with the previously described embodiments, the AMBP-1 is preferably administered with adrenomedullin. Also as previously described, the physiologic effect can be one or more of endothelial cell function, smooth muscle contractility, cardiac output, stroke volume, systemic oxygen delivery, regional blood perfusion, renal function, hepatic function, gut absorptive function, adrenal function, insulin responsiveness, lactic acidosis, hemoconcentration, total peripheral vascular resistance, or IL-10, TNF-$\alpha$, IL-1$\beta$ or IL-6 release.

As with the previously described embodiments, these methods can be used on any mammal including humans, and the AMBP-1 or adrenomedullin can be from any mammalian species. It can also be altered to resist rapid degradation in the mammal, as described above. These methods can also be used with any type of shock, and the AMBP-1 can be administered at any time before initiation of shock, and/or during the initial, compensatory, or progressive stage of the shock.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

It was observed in studies in rats that adrenomedullin (100 nM)+AMBP-1 (50 nM) reduced endotoxin (100 ng/ml)-stimulated release of TNF-$\alpha$ (Wu et al., 2003). This suggests that adrenomedullin is an anti-inflammatory factor. In the current study, the significant rise in serum levels of TNF-$\alpha$, IL-1$\beta$ and IL-6 seen at 20 h after the onset of sepsis in the vehicle-treated animals was significantly blunted in the animals treated with adrenomedullin+AMBP-1. In line with the beneficial effect of adrenomedullin+AMBP-1 on the cardiovascular response, it is probable that down-regulation of proinflammatory cytokines by adrenomedullin+AMBP-1 is one of the mechanisms responsible for the beneficial effects of these agents observed during sepsis. The plasma level of adrenomedullin was found to be reduced at 20 h after CLP in animals treated with adrenomedullin+AMBP-1 as compared with vehicle-treated animals. This apparently paradoxical result is explained by the fact that the available adrenomedullin assay measures only unbound adrenomedullin. Following administration of adrenomedullin+AMBP-1, the fraction of unbound adrenomedullin decreased due to an increase in adrenomedullin bound to AMBP-1.

Materials and Methods

Animal Model of Polymicrobial Sepsis. Polymicrobial sepsis was induced by CLP in male adult Sprague-Dawley rats (300±12 g), Charles River Laboratories, Wilmington, Mass., as described previously (Wichterman et al., 1980). In brief, all experimental rats were fasted overnight but allowed water ad libitum prior to the experiment. Under anesthesia with isoflurane inhalation the cecum was exposed through a 2-cm abdominal midline incision, ligated just distal to the ileocecal valve in order to avoid intestinal obstruction, punctured twice with an 18-gauge needle, squeezed to expel a small amount of fecal material, and the abdominal incision was then closed in two layers. Sham operated rats underwent the same procedure except that the cecum was neither ligated nor punctured. All animals received normal saline (3 ml/100 g body wt.) subcutaneously immediately after the surgery to provide fluid resuscitation. Various parameters were determined at 20 h after CLP (i.e., the late, hypodynamic phase of polymicrobial sepsis). There were six animals in each group. The experiments described here were performed in adherence to the National Institutes of Health guidelines for the use of experimental animals. This project was approved by the Institutional Animal Care and Use Committee of the University of Alabama at Birmingham.

Administration of Adrenomedullin+AMBP-1. Synthetic rat adrenomedullin (Phoenix Pharmaceuticals, Belmont, Calif.) and AMBP-1 (Cortex, San Leandro, Calif.) were co-administered via the femoral venous catheter using a Harvard Pump (Harvard Apparatus, Holliston, Mass.) at 5 h after CLP. Adrenomedullin (12 µg/kg body wt.) and AMBP-1 (40 µg/kg body wt.) were mixed in normal saline to a total volume of 1 ml which was infused over 1 h. This concentration of adrenomedullin+AMBP-1 and infusion rate did not significantly alter mean arterial pressure (MAP) and heart rate (data not shown). Vehicle-treated animals received 1 ml of normal saline instead of adrenomedullin+AMBP-1.

Determination of Cardiac Output and Organ Blood Flow. At 20 h after CLP or sham operation, cardiac output (CO) and regional blood flow were determined by using radioactive microspheres. In brief, both the right femoral artery and vein were cannulated with PE-50 tubing under isoflurane anesthesia. The catheter inserted into the femoral artery was connected to a blood pressure analyzer (Digi-Med, Louisville, Ky.) for the measurement of MAP and heart rate. An additional PE-50 catheter was inserted into the left ventricle via the right carotid artery. Strontium-85-labeled microspheres (DuPont/NEN, Boston, Mass.) were suspended in 15% dextran containing 0.05% Tween-80 surfactant to prevent aggregation and dispersed with a vortex shaker for 3 min. An ~0.2 ml suspension, containing an estimated 150,000 microspheres with an activity of ~4 µCi was infused into the left ventricle over a period of 20 sec at a constant rate. The reference blood sample was withdrawn from the femoral arterial catheter beginning 20 sec before microsphere infusion and continuing for 80 sec at a rate of 0.7 ml/min. At the end of the experiment, the rats were euthanized with an overdose of pentobarbital sodium. Various organs/tissues were harvested, washed with normal saline, and gently blotted on filter paper. The radioactivity in the tissues, reference blood sample and the microspheres remaining in the syringe were counted on a Wallac automatic gamma counter (1480 Wizard, Wallac, Gaithersburg, Md.). CO, blood flow in various organs, stroke volume (SV) and total peripheral resistance (TPR) were calculated.

Determination of Systemic Oxygen Delivery and Hematocrit. Approximately 0.3 ml blood samples were withdrawn from the femoral artery and vein before the injection of microspheres. Oxygen content and hematocrit ($H_{sys}$) were measured using a blood gas analyzer (Radiometer Copenhagen, ABL 700 Series, Denmark). Systemic oxygen delivery ($DO_2$) and oxygen consumption ($VO_2$) were calculated by multiplying CO by arterial oxygen content or the difference between arterial and venous oxygen content, respectively.

Determination of Circulating Levels of Proinflammatory Cytokines. Two ml blood samples were collected in pyrogen/endotoxin free glass tubes at 20 h after CLP via cardiac puncture at least 2 min after the injection of radioactive microspheres. Please note that radioactivity in the collected blood samples was not significantly higher than the background levels. The blood samples were placed on ice for 10 min and centrifuged at 1,200 rpm for 10 min, serum samples were then stored at −70° C. until assayed. Serum levels of TNF-α, IL-1β and IL-6 were measured using enzyme-linked immunosorbent assay kits (PharMingen, San Diego, Calif. for TNF-α, BioSource International, Camarillo, Calif. for IL-1β and IL-6) according to the manufacturer's instructions. The assay range was 0–1000 pg/ml for TNF-α, 0–2000 pg/ml for IL-1β, and 0–2000 pg/ml for IL-6. Please note that samples for IL-1β and IL-6 (not for TNF-α) were diluted by a factor of 1:2 prior to the assay.

Determination of Plasma Levels of Transaminases and Lactate. Additional 1.5 ml blood samples were collected in EDTA-coated test tubes at 20 h after CLP as described above. Plasma was separated immediately by centrifugation and stored at −70° C. until assayed. Plasma levels of alanine aminotransferase (ALT), aspartate aminotransferase (AST), and lactate were measured using Sigma kits (Sigma, St. Louis, Mo.) according to the manufacturer's instructions.

Determination of Plasma Levels of Adrenomedullin. At 20 h after CLP, a radioimmunoassay kit specific for rat adrenomedullin (Peninsula Laboratories, Belmont, Calif.) was used to measure plasma levels of adrenomedullin in various groups of animals according to the procedure provided by the manufacturer and described previously. Briefly, 1.0 ml blood samples were collected in polypropylene tubes containing EDTA (1 mg/ml) and aprotinin (500 KIU/ml). Plasma was separated immediately and stored at −70° C. until assayed. Adrenomedullin was extracted from 0.5 ml plasma on C18 columns eluted with 60% acetonitrile in 1% trifluoroacetic acid. Eluates were evaporated to dryness using a centrifugal concentrator. Samples were dissolved in RIA buffer and then incubated overnight at 4° C. with the antibody raised against rat adrenomedullin. The [$^{125}$I] adrenomedullin was then added for further overnight incubation at 4° C. Free and bound fraction of [$^{125}$I] adrenomedullin were separated by the addition of a secondary antibody and centrifugation. Reactivity of the pellet was then measured. The rat adrenomedullin assay does not have any cross-reactivity with human adrenomedullin, amykin or endothelin-1.

Statistical Analysis. Data are presented as means±SE. One-way analysis of variance (ANOVA) and Tukeys test were employed for comparison among different groups of animals. The differences were considered significant at $p<0.05$.

Results

Effect of Adrenomedullin+AMBP-1 on Hemodynamic Parameters and Systemic Oxygen Delivery and Consumption. It was found that cardiac output (CO) and stroke volume (SV) decreased by 34% ($p<0.05$) and 42% ($p<0.05$), respectively, at 20 h after CLP with the administration of vehicle (normal saline). In contrast, total peripheral resistance (TPR) increased by 64% ($p<0.05$) under such conditions. Animals treated with adrenomedullin +AMBP-1 at 5 h after CLP, however, had CO, SV and TPR value similar to sham-operated animals (no sepsis). In the adrenomedullin+ AMBP-1 treated group, CO was 43% higher ($P<0.05$) than the CO in vehicle-treated animals (Table 1). Similarly, at 20 h after CLP adrenomedullin +AMBP-1-treated animals had systemic $DO_2$ value 35% higher ($p<0.05$) than the vehicle-treated group [which showed a 30% decrease ($p<0.05$) relative to the sham group] (Table 2). Moreover, adrenomedullin+AMBP-1 prevented hemoconcentration at 20 h after CLP (Table 2). In contrast, systemic $VO_2$, MAP, and heart rate were not significantly altered with or without adrenomedullin+AMBP-1 treatment (Table 2).

TABLE 1

Alterations in cardiac output (CO), stroke volume (SV) and total peripheral resistance (TPR) in septic animals treated with vehicle (normal saline) or adrenomedullin + AMBP-1 (AM + AMBP-1) as well as sham-operated animals and at 20 h after CLP.

|  | Sham | CLP + Vehicle | CLP + AM + AMBP-1 |
|---|---|---|---|
| CO (ml/min/100 g BW) | 25.98 ± 1.12 | 17.18 ± 0.98* | 24.56 ± 1.61# |
| SV (µl/beat/100 g BW) | 65.4 ± 4.3 | 38.0 ± 2.1* | 58.2 ± 4.9# |
| TPR (mm Hg/ml/min/ 100 g BW) | 4.09 ± 0.24 | 6.68 ± 0.41* | 4.42 ± 0.25# |

There were six animals in each group. Data are expressed as means ± SE and compared by one-way ANOVA and Tukey's test:
*$P < 0.001$ vs. sham-operated animals;
$P = 0.003$ to $0.001$ vs. CLP animals treated with vehicle.

TABLE 2

Alterations in hemodynamic parameters and systemic oxygen utilization at 20 hours after CLP.

|  | Sham | CLP + Vehicle | CLP + AM + AMBP-1 |
|---|---|---|---|
| Systemic DO$_2$ (ml/min/100 g BW) | 4.90 ± 0.22 | 3.45 ± 0.22* | 4.65 ± 0.25# |
| Systemic VO$_2$ (ml/min/100 g BW) | 0.97 ± 0.10 | 1.05 ± 0.12 | 1.23 ± 0.08 |
| MAP (mmHg) | 105 ± 2 | 113 ± 3 | 107 ± 1 |
| HR (beat/min) | 401 ± 14 | 453 ± 10 | 425 ± 9 |
| H$_{sys-}$ | 43.7 ± 0.5 | 46.6 ± 0.9* | 44.3 ± 0.4# |

Values are presented as means ± SE (n = 6/group) and compared by one-way ANOVA and Tukey's test.
*$P < 0.05$ vs. the sham-operated animals;
$P < 0.05$ vs. the CLP animals treated with vehicle (normal saline).
AM, adrenomedullin;
AMBP-1, adrenomedullin binding protein.

Effect of Adrenomedullin+AMBP-1 on Regional Perfusion. As shown in Table 3, total hepatic blood flow in vehicle-treated animals decreased by 38% (P<0.05) at 20 h after CLP mainly as a result of a 42% decline (P<0.05) in the portal venous component without significant alteration in hepatic arterial blood flow. Administration of adrenomedullin+AMBP-1, however, maintained hepatic perfusion at 20 h after CLP. Similarly, small intestinal and renal perfusion decreased by 54% (P<0.05) and 37% (P<0.05), respectively, at 20h after CLP in vehicle-treated animals. Administration of adrenomedullin+AMBP-1, however, prevented hypoperfusion in the gut and kidneys. Unlike the above organs, cardiac blood flow (i.e., coronary arterial blood flow) did not decrease at 20 h after CLP in vehicle-treated animals and adrenomedullin+AMBP-1 did not significantly increase cardiac blood flow (Table 3).

TABLE 3

Alterations in regional blood flow at 20 hours after CLP.

|  | Sham | CLP + Vehicle | CLP + AM + AMBP-1 |
|---|---|---|---|
| Hepatic Arterial BF (ml/min/100 g tissue) | 27.0 ± 5.6 | 24.1 ± 3.6 | 32.5 ± 4.2 |
| Portal BF (ml/min/100 g tissue) | 155.7 ± 18.5 | 89.7 ± 15.4* | 167.0 ± 18.5# |
| Total Hepatic BF (ml/min/100 g tissue) | 182.7 ± 19.0 | 113.8 ± 16.2* | 199.5 ± 20.0# |
| Small Intestinal BF (ml/min/100 g tissue) | 188.9 ± 20.7 | 113.3 ± 18.6* | 285.7 ± 18.1*# |
| Renal BF (ml/min/100 g tissue) | 546.4 ± 22.9 | 393.4 ± 24.5* | 558.2 ± 8.6# |
| Cardiac BF (ml/min/100 g tissue) | 727.2 ± 144.0 | 452.1 ± 64.9 | 671.9 ± 139.9 |

Values are represented as means ± SE (n = 6/group) and compared by one-way ANOVA and Tukey's test.
*$P < 0.05$ vs. the sham-operated animals;
$P < 0.05$ vs. the CLP animals treated with vehicle (normal saline).
AM, adrenomedullin;
AMBP-1, adrenomedullin binding protein-1;
BF, blood flow.

Effect of Adrenomedullin+AMBP-1 on Circulating Levels of Proinflammatory Cytokines. It was found that serum levels of TNF-α, IL-1β and IL-6 increased by 12, 15 and 7 fold, respectively, at 20 h after CLP in vehicle-treated animals. Administration of adrenomedullin+AMBP-1, however, significantly reduced serum levels of TNF-α, IL-1β and IL-6 at 20 h after CLP. In contrast, administration of adrenomedullin+AMBP-1 did not alter circulating levels of these cytokines in sham-operated animals (Table 4).

TABLE 4

Alterations in serum TNF-α, IL-1β and IL-6 in septic animals treated with vehicle (normal saline) or adrenomedullin + AMBP-1 (AM + AMBP), as well as sham-operated animals at 20 hours after CLP.

|  | Sham | CLP + Vehicle | CLP + AM + AMBP-1 |
|---|---|---|---|
| TNF-α (pg/ml) | 20.5 ± 8.4 | 273.2 ± 61.8* | 46.9 ± 12.7# |
| IL-1β (pg/ml) | 11.4 ± 3.9 | 183.9 ± 58.1* | 43.5 ± 12.7# |
| IL-6 (pg/ml) | 274.5 ± 16.4 | 2317.8 ± 310.4* | 1314.9 ± 186.6*# |

There were six animals in each group. Data are expressed as means ± SE (n = 6/group) and compared by one-way ANOVA and Tukey's test:
*$P = 0.008$ to $0.001$ vs. the sham-operated animals;
$P = 0.029$ to $0.002$ vs. the CLP animals treated with vehicle.

Effect of Adrenomedullin+AMBP-1 on Plasma Levels of Transaminases and Lactate. It was found that plasma levels of ALT and AST increased by 3.2 and 2.4 fold, respectively, at 20 h after CLP in vehicle-treated animals (p<0.05). Administration of adrenomedullin+AMBP-1, however, reduced the extent of ALT and AST elevation by 46% and 52% (p<0.05), respectively, as compared to vehicle-treated animals. ALT and AST levels in septic animals treated with adrenomedullin+AMBP-1 and in sham-operated animals were not statistically different. Similarly, circulating levels of lactate increased by 168% (P<0.05) at 20 h after CLP in vehicle-treated animals, however, administration of adrenomedullin+AMBP-1 attenuated the increase in lactate (P<0.05) (Table 5).

TABLE 5

Alterations in plasma levels of alanine aminotransferase (ALT), aspartate aminotransferase (AST) and plasma levels of lactate in septic animals treated with vehicle (normal saline) or adrenomedullin + AMBP-1 (AM + AMBP-1), as well as sham-operated animals at 20 hours after CLP.

|  | Sham | CLP + Vehicle | CLP + AM + AMBP-1 |
|---|---|---|---|
| ALT (SF U/ml) | 20.0 ± 2.0 | 83.7 ± 9.3* | 44.7 ± 3.4# |
| AST (SF U/ml) | 48.8 ± 3.4 | 168.0 ± 16.9* | 81.0 ± 7.6# |
| Lactate (mg/dl) | 18.5 ± 2.2 | 51.0 ± 4.2* | 27.0 ± 2.9# |

There were six animals in each group. Data are expressed as means ± SE and compared by one-way ANOVA and Tukey's test:
*P < 0.001 vs. the sham-operated animals;
P < 0.001 vs. the CLP animals treated with vehicle.

Effect of Adrenomedullin+AMBP-1 on Plasma Levels of Adrenomedullin at 20 h after CLP. It was found that plasma levels of adrenomedullin increased by 146% at 20 h after CLP in vehicle-treated animals (P<0.05). The plasma levels of adrenomedullin in adrenomedullin+AMBP-1-treated animals showed a statistically insignificant rise compared to the sham group, but it was significantly lower than the adrenomedullin level in vehicle-treated group (Table 6).

TABLE 6

Alterations in plasma levels of adrenomedullin in septic animals treated with vehicle (normal saline) or adrenomedullin + AMBP-1 (AM + AMBP-1), as well as sham-operated animals at 20 hours after CLP.

|  | Sham | CLP + Vehicle | CLP + AM + AMBP-1 |
|---|---|---|---|
| Plasma AM Levels (pg/ml) | 173 ± 14 | 426 ± 31* | 257 ± 19*# |

There were six animals in each group. Data are expressed as means ± SE and compared by one-way ANOVA and Tukey's test.
*P < 0.001 vs. the sham-operated animals;
P < 0.001 vs. the CLP animals treated with vehicle.

Administration of Adrenomedullin+AMBP-1 Simultaneously with the Initiation of Sepsis. Synthetic rat adrenomedullin (Phoenix Pharmaceuticals, Belmont, Calif.) was administered continuously via a jugular vein using an Alzet mini-osmotic pump (Durect, Cupertino, Calif.) for the entire duration of the study. Rats were fasted overnight but allowed water ad libitum prior to the experiment. The fasted animals were anesthetized with isoflurane inhalation and a 1.0 cm incision was made in the neck. A 200 µl mini-osmotic pump was prefilled with adrenomedullin solution (dissolved with sterile normal saline to 20 µg/ml) and connected to a silastic catheter (size 0.030" I.D., 0.065" O. D., Baxter, McGaw Park, Ill.). The prefilled pump was then primed in sterile normal saline for 2 h at 37° C. before implantation. The prefilled and primed mini-osmotic pump was then implanted subcutaneously in the rat 3 h prior to induction of sepsis and the silastic catheter was inserted into the right jugular vein for continuous infusion of adrenomedullin at a constant rate of 8 µl/h for 23 h (total dosage 12 µg/kg body wt). Following the close of the neck incision, CLP was performed 3 h after the implantation of the pump. The right femoral vein was then cannulated using PE-50 tubing and 1 ml human AMBP-1 solution (containing 12 µg AMBP-1, Cortex, San Leandro, Calif.) was infused via the femoral venous catheter using a Harvard Pump (Harvard Apparatus, Holliston, Mass.) at a rate of 0.05 ml/min for a period of 20 min. The dose of AMBP-1 administered was approximately 40 µg/kg body wt. Vehicle-treated animals received sterile normal saline instead of adrenomedullin+AMBP-1. In additional groups of septic animals, either AM alone (12 µg/kg body wt.) or AMBP-1 alone (40 µg/kg body wt.) was administered, as described above, in order to determine the effect of each individual agent on septic cardiovascular responses. It should be noted that adrenomedullin at a dose of 12 µg/kg body wt. was used since it increases plasma adrenomedullin to a level which at least doubles adrenomedullin concentration observed during sepsis (600–700 pg/ml at 10–20 h after CLP). The dosage of AMBP-1 used in this study was based the preliminary study in which $2-5H10^{-9}$ M AMBP-1 significantly enhanced adrenomedullin-induced vascular relaxation.

Effects of Adrenomedullin+AMBP-1 on the Survival Rate. The survival rate after CLP and cecal excision with vehicle administration was 57% at days 2–6 and decreased to 43% at days 7–10. Administration of adrenomedullin+AMBP-1 at 5 h after CLP, however, reduced the mortality rate to 7% at days 7–10 (P<0.05 on day 10) (Table 7). The results also show that, when administered simultaneously with exposure to sepsis, adrenomedullin+AMBP-1 improved CO, $DO_2$, organ blood flow, and reduces TPR, ALT, AST and lactate at 20 h after CLP (data not shown).

TABLE 7

Effects of Adrenomedullin + AMBP-1 on the survival rate (%) at 10 days after cecal ligation and puncture and cecal excision with vehicle treatment (CLPE + Vehicle) and cecal ligation and puncture with adrenomedullin + AMBP-1 treatment (CLPE + AM + AMBP-1).

| | Days after CLPE | | | | | | | | | |
|---|---|---|---|---|---|---|---|---|---|---|
| | 1 | 2 | 3 | 4 | 5 | 6 | 7 | 8 | 9 | 10 |
| CLPE + Vehicle | 85.7 | 57.1 | 57.1 | 57.1 | 57.1 | 57.1 | 42.9 | 42.9 | 42.9 | 42.9 |
| CLPE + AM + AMBP-1 | 100 | 100 | 100 | 100 | 100 | 100 | 92.9 | 92.9 | 92.9 | 92.9 |

There were 14 animals in each group, and the data were analyzed by the Kaplan-Meier method and compared by the logrank test. P < 0.05 vs. CLPE + Vehicle.

The above data and other supporting data are also found in Yang et al., 2002a; Yang et al., 2002b; and Wu et al., 2000, the contents of which are incorporated in their entirety by reference.

EXAMPLE 2

Modulation of Vascular Responsiveness to Adrenomedullin after Hemorrhagic Shock: Beneficial Effects of Adrenomedullin and Adrenomedullin Binding Protein-1 (AMBP-1).

Introduction. Our preliminary results indicate that vascular responsiveness to adrenomedullin is depressed after hemorrhage and resuscitation. Downregulation of AMBP-1 expression appears to be responsible for this hyporesponsiveness. In addition, AMBP-1 attenuates vascular adrenomedullin hyporesponsiveness induced by hemorrhage under in vivo conditions.

Hypothesis. Administration of adrenomedullin and AMBP-1 improves cardiovascular function after hemorrhagic shock under in vivo conditions.

Methods. Male rats (275–325 g) were bled to and maintained at a mean blood pressure of 40 mm Hg for 90 min. There were then resuscitated with four times the volume of shed blood in the form of Ringer's lactate over 60 min. At 15 min after the beginning of resuscitation in hemorrhaged animals, adrenomedullin (12 µg/kg body weight) and AMBP-1 (40 µg/kg body weight) or vehicle (PBS, 1 ml) were administered via the femoral venous catheter over a period of 45 min. At 4 h post-resuscitation, left ventricular contractility parameters such as the maximal rates of ventricular pressure increase (+dP/dt$_{max}$, mm Hg/sec) and decrease (−dP/dt$_{max}$) were determined. Cardiac output (CO, ml/min/100 g body weight) and organ blood flow (BF, ml/min/100 g tissue) were measured using $^{141}$Cr-microspheres.

Results. As indicated in Table 8, +dP/dt$_{max}$, −dP/dt$_{max}$, CO and BF in the gut, liver and kidneys decreased significantly at 4 h after resuscitation. Treatment with adrenomedullin+AMBP-1 markedly increased the above parameters.

($10^{-7}$ M) and AMBP-1 ($2 \times 10^{-8}$ M) was determined by using an isolated gut preparation. Blood and tissue samples were collected and AMBP-1 levels were measured by Western blotting. AMBP-1 (gut and liver) and adrenomedullin receptor complex (gut) mRNA expression was measured by RT-PCR.

Results. The data in FIG. 1 indicate that adrenomedullin-induced vascular relaxation decreased significantly, which was markedly improved by addition of AMBP-1. Hemorrhage-induced adrenomedullin hyporesponsiveness was accompanied by decreased AMBP-1 levels in plasma and gut and its down-regulated gene expression in the gut and liver (Table 9). The altered vascular adrenomedullin responsiveness after hemorrhage is not due to adrenomedullin receptors since adrenomedullin receptor components did not change under such conditions (data not shown).

TABLE 9

|  |  | Sham | 1.5 h Rs |
| --- | --- | --- | --- |
| AMBP-1 protein | Plasma ($10^5$ pixels/400 µg protein) | 5.69 ± 0.74 | 3.07 ± 0.39* |
|  | Gut ($10^5$ pixels/200 µg protein) | 3.78 ± 0.89 | 0.82 ± 0.26* |
| AMBP-1 mRNA | Gut (AMBP-1/G3PDH) | 1.57 ± 0.20 | 0.81 ± 0.04* |
|  | Liver (AMBP-1/G3PDH) | 0.41 ± 0.03 | 0.22 ± 0.02* |

(Mean ± SE, n = 5–6/group, Student's t-test: *P < 0.05 vs. Sham)

Conclusion. The decreased AMBP-1 expression and release after hemorrhage rather than alterations in adrenom-

TABLE 8

|  | +dP/dt$_{max}$ | −dP/dt$_{max}$ | CO | gut BF | Liver BF | Kidneys BF |
| --- | --- | --- | --- | --- | --- | --- |
| Sham | 10477 ± 563 | 7750 ± 797 | 27 ± 0.5 | 152 ± 16.9 | 164 ± 11.7 | 652 ± 73.1 |
| Vehicle | 8051 ± 679* | 4145 ± 429* | 21 ± 0.4 | 78 ± 17.7 | 110 ± 12.9* | 195 ± 27.1* |
| AM + AMBP-1 | 10518 ± 709# | 6128 ± 361# | 29 ± 1.2# | 146 ± 9.6# | 188 ± 1.4# | 423 ± 58.5*# |

AM = adrenomedullin.
Values are means ± SE, n = 5/group. ANOVA and Student-Newman-Keuls,
*= P < 0.05 vs. Sham,
= P < 0.05 vs. Vehicle Conclusions. Since adrenomedullin+AMBP-1 improves left ventricular performance, CO and organ blood flow, administration of these agents appears to be a useful approach for restoring and maintaining cardiovascular stability after severe hemorrhagic shock.

EXAMPLE 3

Mechanisms Responsible for the Reduced Microvascular Responsiveness to Adrenomedullin after Hemorrhage: the Central Role of Adrenomedullin Binding Protein-1 (AMBP-1).

Irreversible hypovolemia remains a major clinical problem. Preliminary studies indicate that administration of adrenomedullin+AMBP-1 after hemorrhage improves cardiovascular function despite the increased levels of adrenomedullin. The aim of this study was to determine whether vascular responsiveness to adrenomedullin is reduced after hemorrhage and, if so, to elucidate the mechanism responsible for adrenomedullin hyporesponsiveness.

Methods. Male rats (275–325 g) were bled to and maintained at a BP of 40 mm Hg for 90 min. They were then resuscitated with 4 times the volume of shed blood in the form of Ringer's lactate over 60 min. At 1.5 h post-resuscitation (Rs), the vascular response to adrenomedullin edullin receptors are responsible for the reduced microvascular responsiveness to adrenomedullin. Since AMBP-1 improves vascular adrenomedullin hyporesponsiveness, administration of adrenomedullin in combination with AMBP-1 will be useful to prevent organ injury and death after severe hypovolemia and resuscitation.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method of treating a mammal in shock or at risk for shock, the shock having an initial stage, a compensatory stage, and a progressive stage, the method comprising administering an adrenomedullin binding protein-1 (AMBP-1) to the mammal in sufficient amount to reduce a physiologic effect of the shock.

2. The method of claim 1, further comprising administration of an adrenomedullin to the mammal.

3. The method of claim 2, wherein the adrenomedullin and the AMBP-1 are from same species as the mammal.

4. The method of claim 2, wherein the adrenomedullin and the AMBP-1 are derived from the same species.

5. The method of claim 1, wherein the mammal is a human.

6. The method of claim 1, wherein the shock is hypovolemic shock.

7. The method of claim 6, wherein the hypovolemic shock is hemorrhagic shock.

8. The method of claim 1, wherein the shock is traumatic shock.

9. The method of claim 1, wherein the physiologic effect is selected from the group consisting of endothelial cell function, smooth muscle contractility, cardiac output, stroke volume, systemic oxygen delivery, regional blood perfusion, renal function, hepatic function, gut absorptive function, adrenal function, insulin responsiveness, lactic acidosis, hemoconcentration, total peripheral vascular resistance, and IL-10, TNF-$\alpha$, IL-1$\beta$ or IL-6 release.

10. The method of claim 1, wherein the AMBP-1 is administered at 0.2–100 µg/kg body weight.

11. The method of claim 10, further comprising administration of an adrenomedullin at 0.1–50 µg/kg body weight.

12. The method of claim 1, wherein the AMBP-1 is administered within 90 minutes of the initiation of the shock.

13. The method of claim 1, wherein the AMBP-1 is administered before initiation of the shock.

14. The method of claim 1, wherein the AMBP-1 is administered during the initial or the compensatory stage of shock.

15. The method of claim 1, wherein the AMBP-1 is administered during the progressive stage of shock.

16. The method of claim 1, further comprising administering at least one other agent that reduces a physiological effect of the shock.

17. The method of claim 16, wherein each such other agent is selected from the group consisting of a vasodilator, a vasopressor, a corticosteroid, an antibiotic, and an opiate.

18. A method of preventing or treating a physiologic effect of shock in a mammal, the method comprising administering to the mammal an adrenomedullin binding protein-1 (AMBP-1) in sufficient amount to reduce the physiologic effect of the shock.

19. The method of claim 18, further comprising administration of an adrenomedullin to the mammal.

20. The method of claim 18, wherein the physiologic effect is selected from the group consisting of endothelial cell function, smooth muscle contractility, cardiac output, stroke volume, systemic oxygen delivery, regional blood perfusion, renal function, hepatic function, gut absorptive function, adrenal function, insulin responsiveness, lactic acidosis, hemoconcentration, total peripheral vascular resistance, and IL-10, TNF-$\alpha$, IL-1$\beta$ or JL-6 release.

* * * * *

UNITED STATES PATENT AND TRADEMARK OFFICE
CERTIFICATE OF CORRECTION

PATENT NO. : 6,884,781 B2
DATED : April 26, 2005
INVENTOR(S) : Ping Wang

It is certified that error appears in the above-identified patent and that said Letters Patent is hereby corrected as shown below:

Column 16,
Lines 24-31, please amend Claim 20 from:
20. The method of claim 18, wherein the physiologic effect is selected from the group consisting of endothelial cell function, smooth muscle contractility, cardiac output, stroke volume, systemic oxygen delivery, regional blood perfusion, renal function, hepatic function, gut absorptive function, adrenal function, insulin responsiveness, lactic acidosis, hemoconcentration, total peripheral vascular resistance, and IL-10, TNF-alpha, IL-1Beta or JL-6 release.
to:
20. The method of claim 18, wherein the physiologic effect is selected from the group consisting of endothelial cell function, smooth muscle contractility, cardiac output, stroke volume, systemic oxygen delivery, regional blood perfusion, renal function, hepatic function, gut absorptive function, adrenal function, insulin responsiveness, lactic acidosis, hemoconcentration, total peripheral vascular resistance, and IL-10, TNF-α, IL-1β or IL-6 release.

Signed and Sealed this

Ninth Day of August, 2005

JON W. DUDAS
*Director of the United States Patent and Trademark Office*

UNITED STATES PATENT AND TRADEMARK OFFICE
CERTIFICATE OF CORRECTION

PATENT NO. : 6,884,781 B2
APPLICATION NO. : 10/729193
DATED : April 26, 2005
INVENTOR(S) : Ping Wang Page 1 of 1

It is certified that error appears in the above-identified patent and that said Letters Patent is hereby corrected as shown below:

In Column 1, lines 10-18,

"STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant Nos. RO1 GM57468, GM53008, and KO2 AI01461, awarded by the National Institutes of Health."

should read

--STATEMENT OF GOVERNMENT SUPPORT

This invention was made with government support under grants GM53008, GM57468 and KO2 AI01461 awarded by the National Institutes of Health. The government has certain rights in the invention.--

Signed and Sealed this
Twenty-third Day of August, 2011

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 6,884,781 B2 |
| APPLICATION NO. | : 10/729193 |
| DATED | : April 26, 2005 |
| INVENTOR(S) | : Ping Wang |

It is certified that error appears in the above-identified patent and that said Letters Patent is hereby corrected as shown below:

In the Specification

Column 1, Lines 13-18, Delete:
"The U.S. Government has a paid-up license in this invention and the right in limited circumstances to require the patent owner to license others on reasonable terms as provided for by the terms of Grant Nos. RO1 GM57468, GM53008, and KO2 A101461, awarded by the National Institutes of Health."

And Insert:
--This invention was made with government support under AI001461 and GM057468 awarded by the National Institutes of Health. The government has certain rights in the invention.--

Signed and Sealed this
Twenty-first Day of November, 2023

Katherine Kelly Vidal
*Director of the United States Patent and Trademark Office*